(12) United States Patent
Chao et al.

(10) Patent No.: US 10,251,886 B1
(45) Date of Patent: Apr. 9, 2019

(54) 4-ANILINOQUINAZOLINE DERIVATIVE AND ALBUMIN CONJUGATES THEREOF

(71) Applicant: National Chiao Tung University, Hsinchu (TW)

(72) Inventors: Jui-I Chao, Zhubei (TW); Chin-Piao Chen, Hualien (TW); Kuang-Kai Liu, Taoyuan (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 15/903,494

(22) Filed: Feb. 23, 2018

(30) Foreign Application Priority Data

Feb. 9, 2018 (TW) .............................. 107104617 A (51) Int. Cl.
*A61K 47/64* (2017.01)
*A61P 35/00* (2006.01)
*A61K 31/517* (2006.01)

(52) U.S. Cl.
CPC .......... *A61K 31/517* (2013.01); *A61K 47/643* (2017.08); *A61P 35/00* (2018.01)

(58) Field of Classification Search
CPC .............................. A61K 31/517; A61P 36/00
USPC ...................................................... 514/266.1
See application file for complete search history.

(56) References Cited

U.S. PATENT DOCUMENTS 5,439,686 A    8/1995   Desai et al.
6,652,884 B2   11/2003  Falciani

OTHER PUBLICATIONS

Boobalan et al., "Synthesis and biological assay of erlotinib analogues and BSA-conjugated erlotinib analogue", Bioorganic & Medicinal Chemistry Letters, vol. 27, No. 8, pp. 1784-1788 (2017).*

* cited by examiner

*Primary Examiner* — Kevin E Weddington
(74) *Attorney, Agent, or Firm* — Cesari and McKenna, LLP (57) ABSTRACT a pharmaceutical composition for preventing, treating, or ameliorating one or more symptoms of a malignant tumor associated with EGFR mutation and/or K-RAS mutation is provided. The pharmaceutical composition includes a 4-anilinoquinazoline derivative having a formula (I)

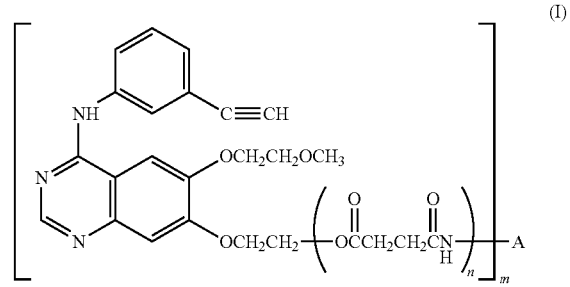

where A is iodine when m is 1 and n is zero, or A is albumin when m is an integral ranging from 1 to 7 and n is 1.

7 Claims, 4 Drawing Sheets

FIG.4 where BSA is bovine serum albumin.

4-ANILINOQUINAZOLINE DERIVATIVE AND ALBUMIN CONJUGATES THEREOF

CROSS-REFERENCE TO RELATED APPLICATION

This application claims priority from Taiwanese invention patent application no. 107104617, filed on Feb. 9, 2018.

FIELD

The disclosure relates to a pharmaceutical composition, more particularly to a pharmaceutical composition for preventing, treating, or ameliorating one or more symptoms of a malignant tumor associated with EGFR mutation and/or K-RAS mutation.

BACKGROUND

Lung carcinoma is one of the most common and serious types of cancer. The two main types are small-cell lung carcinoma (SCLC) and non-small-cell lung carcinoma (NSCLC). A vast majority (80%-85%) of cases of lung cancer are NSCLC. Epidermal growth factor receptor (EGFR) which possesses tyrosine kinase activity is mutated and/or overexpressed in many human cancers, such as NSCLC. Therefore, receptor tyrosine kinase inhibitors are useful as selective inhibitors of the growth of mammalian cancer cells.

Erlotinib is a first-line drug for treating NSCLC, and is a well-known EGFR tyrosine kinase inhibitor (EGFR-TKI), which competes with ATP for binding to the tyrosine kinase domain of the EGFR to suppress EGFR activity, to thereby block signaling in survival and proliferation of cancer cells. According to researches on lung cancer, effects of Erlotinib in patients are associated with EGFR mutations, and the efficacy of Erlotinib varies among different sensitive EGFR mutations. NSCLC patients with deletion mutations in exon 19 or leucine-to-arginine substitution at amino acid position 858 (L858R) in exon 21 are sensitive to Erlotinib treatment. In addition, Erlotinib specifically targets EGFR mutations, and is thus less harmful to normal cells.

However, it is recognized that the efficacy of Erlotinib is of limited duration about 1-2 years owing, in large part, to the emergence of drug resistance conferred by a second point mutation in the EGFR of the cancer cells. The threonine-790 to methionine (T790M) point mutation is found in approximately 50% of all NSCLC patients at the time of acquired resistance to EGFR-TKI therapy. T790M point mutation affects the ATP binding pocket of the EGFR kinase domain, resulting in inhibiting binding of EGFR and EGFR-TKI drug (Erlotinib). Furthermore, it is reported that the resistance to EGFR-TKI drug might be associated with K-RAS mutations in NSCLC patients.

SUMMARY

Therefore, an object of the disclosure is to provide a novel pharmaceutical composition for preventing, treating, or ameliorating one or more symptoms of a malignant tumor, such as non-small-cell lung carcinoma (NSCLC), associated with EGFR mutation and/or K-RAS mutation.

According to the disclosure, a pharmaceutical composition for preventing, treating, or ameliorating one or more symptoms of a malignant tumor associated with EGFR mutation and/or K-RAS mutation is provided. The pharmaceutical composition includes a 4-anilinoquinazoline derivative having a formula (I)

(I)

where A is iodine when m is 1 and n is zero, or A is albumin when m is an integral ranging from 1 to 7 and n is 1.

BRIEF DESCRIPTION OF THE DRAWINGS

Other features and advantages of the disclosure will become apparent in the following detailed description of the embodiment(s) with reference to the accompanying drawings, in which.

DETAILED DESCRIPTION

A pharmaceutical composition according to the disclosure is used for preventing, treating, or ameliorating one or more symptoms of a malignant tumor associated with EGFR mutation and/or K-RAS mutation.

The pharmaceutical composition includes a 4-anilinoquinazoline derivative having a formula (I)

(I)

where A is iodine when m is 1 and n is zero, or A is albumin when m is an integral ranging from 1 to 7 and n is 1. A covalent bond is formed between a 4-anilino- quinazoline moiety and A (iodine or albumin). In addition, the number of m means the number of the 4-anilinoquinazoline moieties bonded to A. For example, when A is albumin and m is 2,4-anilinoquinazoline derivative has a formula (IV)

(IV)

Preferably, the albumin is serum albumin. Non-limiting examples of serum albumin may include bovine serum albumin (BSA), human serum albumin (HSA).

When A is iodine, m is 1 and n is zero, 4-anilinoquinazoline derivative has a formula (II)

(II)

When A is albumin, m is an integral ranging from 1 to 7, and n is 1,4-anilinoquinazoline derivative has a formula (III)

(III)

Preferably, m is 7.

Preferably, the pharmaceutical composition is for preventing, treating, or ameliorating one or more symptoms of non-small-cell lung carcinoma (NSCLC).

Preferably, the pharmaceutical composition further includes a pharmaceutically acceptable vehicle. The pharmaceutically acceptable vehicle may include one or more of following vehicles: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposome, etc. The selection of the pharmaceutically acceptable vehicle may be readily determined by the skilled artisan.

The embodiments of the disclosure will now be explained in more detail below by way of the following examples and comparative examples.

A process for synthesizing a 4-anilinoquinazoline derivative of Comparative Example 1 is shown by Scheme 1:

[Scheme 1]

Isovanillin

Compound 1

Compound 2

Compound 3

Compound 4

Intermediate compound 1

Comparative Example 1 where Bn is a benzyl group.

Compound 1

3-hydroxy-4-methoxybenzonitrile

Isovanillin (12.4 g, 81.5 mmol), sodium formate (13.3 g, 195.6 mmol), and formic acid (65.0 mL) was heated to 85° C., and then hydroxylamine hydrochloride (7.9 g, 114.1 mmol) was further added portionwise within 30 minutes to obtain a mixture. The mixture was heated at 85° C. for overnight. Next, the mixture was cooled to room temperature and poured to a saturated sodium chloride aqueous solution (300 mL), followed by filtration and water washing to collect a solid product. Thereafter, the solid product was dissolved in ether and then dried over $MgSO_4$, and the solvent was removed under reduced pressure on a rotary evaporator and the residue obtained was further dried under high vacuum to give a white solid product (10.3 g, 85% yield). The spectrum analysis for the white solid product obtained by the above procedures is: $^1$H NMR (400 MHz, $CDCl_3$), δ (ppm): 7.21-7.18 (dd, J=2.0, 8.4 Hz, 1H), 7.16-7.15 (d, J=2.0 Hz, 1H), 5.80 (br, 1H), 3.95 (s, 3H); $^{13}$C NMR (100.6 MHz, $CDCl_3$), δ (ppm): 150.2, 145.9, 125.6, 119.0, 117.6, 110.8, 104.6, 56.16. The white solid product obtained was confirmed to be Compound 1 (3-hydroxy-4-methoxybenzonitrile).

Compound 2

3-(benzyloxy)-4-methoxybenzonitrile

Compound 1 (5.0 g, 33.5 mmol) was dissolved in acetonitrile (50.0 mL), and then potassium carbonate (9.3 g, 67.0 mmol) and benzyl bromide (6.7 mL, 58.7 mmol) were further added to obtain a mixture. The mixture was refluxed for 1.5 hours, and then cooled and filtered to collect a filtrate. The filtrate was evaporated under reduced pressure, taken up in ethyl acetate (EtOAc), and water-washed. The aqueous layer was extracted again with EtOAc, and the combined EtOAc layer was dried over $MgSO_4$, followed by evaporation to obtain a crude product. The crude product was purified by column chromatography (230-400 mesh silica gel, 25-30% EtOAc/Hexane) to obtain a white solid (8.0 g, 99% yield). The spectrum analysis for the white solid obtained by the above procedures is: $^1$H NMR (400 MHz, $CDCl_3$), δ(ppm): 7.43-7.31 (m, 5H), 7.29-7.27 (dd, J=8.2, 1.9 Hz, 1H), 7.10 (d, J=1.9 Hz, 1H), 6.92-6.90 (d, J=8.2 Hz, 1H), 5.14 (s, 2H), 3.92 (s, 3H); $^{13}$C NMR (100.6 MHz, $CDCl_3$), δ (ppm): 153.5, 148.2, 135.9, 128.7, 128.3, 127.3, 126.8, 119.2, 126.8, 119.2, 116.5, 11.6, 103.7, 71.2, 56.1. The white solid obtained was confirmed to be Compound 2 (3-(benzyloxy)-4-methoxybenzonitrile).

Compound 3

5-(benzyloxy)-4-methoxy-2-nitrobenzonitrile

A solution including Compound 2 (5.0 g, 20.8 mmol) and glacial acetic acid (20.0 mL) was added dropwise to concentrated nitric acid (70%, 50.0 mL) in an ice bath to obtain a mixture. Once the addition finished, the mixture was stirred for further 1 hour, and then was poured into water and filtered to collect a precipitate followed by water washing to obtain a solid. The solid was dissolved in EtOAc to obtain a mixture solution. Thereafter, the mixture solution was washed with water, a sodium hydroxide aqueous solution (2N), and brine, and then dried over $MgSO_4$, and evaporated to obtain a pale yellowish white solid (4.7 g, 80% yield). The spectrum analysis for the pale yellowish white solid obtained by the above procedures is: $^1$H NMR (400 MHz, $CDCl_3$), δ (ppm): 7.80 (s, 1H), 7.42-7.38 (m, 5H), 7.23 (s, 1H), 5.25 (s, 2H), 4.02 (s, 3H); $^{13}$C NMR (100.6 MHz, $CDCl_3$), δ (ppm): 152.7, 152.4, 142.9, 134.4, 129.0, 128.9, 127.4, 117.1, 115.5, 108.1, 100.6, 71.8, 56.8. The pale yellowish white solid obtained was confirmed to be Compound 3 (5-(benzyloxy)-4-methoxy-2-nitrobenzonitrile).

Compound 4

2-amino-5-(benzyloxy)-4-methoxybenzonitrile

Concentrated hydrochloric acid (10.0 mL) and acetic acid (35.0 mL) were added to tin(II) chloride (anhydrous, $SnCl_2$, 5.0 g, 26.4 mmol) to obtain a first solution. Thereafter, a second solution including dichloromethane (DCM, 30.0 mL) and Compound 3 (2.5 g, 8.7 mmol) was added to the firsts solution, and stirred at 60° C. for 1 hour, followed by cooling to room temperature to obtain a mixture solution. The pH value of the mixture solution was adjusted to 10 by addition of a sodium hydroxide aqueous solution (2M). Next, the mixture solution was extracted with dichloromethane, dried over $MgSO_4$, and evaporated to obtain a crude product. The crude product was purified by column chromatography (70-230 mesh, silica gel, 40% EtOAc/Hexane) to obtain an off-white solid (1.6 g, 73% yield). The spectrum analysis for the off-white solid obtained by the above procedures is: $^1$H NMR (400 MHz, $CDCl_3$), δ (ppm): 7.41-7.29 (m, 5H), 6.81 (s, 1H), 6.23 (s, 1H), 5.01 (s, 2H), 4.18 (b, 2H), 3.85 (s, 3H); $^{13}$C NMR (100.6 MHz, $CDCl_3$), δ (ppm): 155.5, 146.6, 140.7, 136.6, 128.6, 128.1, 127.5, 118.1, 117.2, 99.1, 86.4, 72.2, 55.9. The off-white solid obtained was confirmed to be Compound 4 (2-amino-5-(benzyloxy)-4-methoxybenzonitrile).

Comparative Example 1 (CE1)

6-(benzyloxy)-N-(3-ethynylphenyl)-7-methoxyquinazolin-4-amine

Dimethylformamide dimethylacetal (4 mL) was added to Compound 4 (1.0 g, 3.9 mmol) to obtain a first mixture, and the first mixture was refluxed for 2 hours. Then, the solvent in the mixture was removed by evaporation under high vacuum using rotavapor for drying the mixture for 0.5 hour to obtain a brown residue. Acetic acid (AcOH, 10.0 mL) and 3-ethynylaniline (0.48 mL, 4.3 mmol) were successively added to the brown residue, and and refluxed at 130° C. for 1 hour to obtain a second mixture. The second mixture was then cooled to room temperature and filtered to collect a solid precipitate, followed by water washing to obtain a crude product. The crude product was dissolved in ethyl acetate, dried over $MgSO_4$, evaporated, and dried in high vacuum to obtain a white solid (1.4 g, 93% yield). The spectrum analysis for the white solid obtained by the above procedures is: $^1$H NMR (400 MHz, $CDCl^3$), δ (ppm): 8.66 (s, 1H), 7.78 (s, 1H), 7.67 (d, J=7.9 Hz, 1H), 7.39-7.24 (m, 9H), 7.15 (s, 1H), 5.13 (s, 2H), 3.96 (s, 3H), 3.08 (s, 1H); $^{13}$C NMR (100.6 MHz, $CDCl_3$), δ (ppm): 156.2, 155.4, 153.6, 148.6, 147.7, 138.7, 138.7, 135.9, 129.0, 128.7, 128.3, 127.8, 127.4, 125.0, 122.8, 122.2, 109.0, 108.0, 83.3, 77.5, 71.4, 56.2; LRMS-EI$^+$ (m/z): 382 ([M+H]$^+$, 25), 381 ([M]$^+$, 100), 380 ([M−H]$^+$, 28), 290(28), 275(22), 258(19), 246(13), 230(9), 219(5), 156(4), 91 (22); HRMS-TOF-ES$^+$ (m/z): [M+H]$^+$ calculated for $C_{24}H_{20}H_3O_2$, 382.1556, found: 382.1554. The white solid obtained was confirmed to be a 4-anilinoquinazoline derivative of CE1 (6-(benzyloxy)-N-(3-ethynylphenyl)-7-methoxyquinazolin-4-amine). The spectrum analysis for the brown residue obtained in the above procedures is: 1H NMR (400 MHz, $CDCl_3$), δ (ppm): 7.55 (s, 1H), 7.41-7.26 (m, 5H), 6.96 (s, 1H), 6.46 (s, 1H), 5.07 (s, 2H), 3.89 (s, 3H), 3.05 (s, 6H). The brown residue obtained was confirmed to be Intermediate compound 1 (formimidamide) shown in Scheme 1.

A process for synthesizing a 4-anilinoquinazoline derivative of Comparative Example 2 is shown by Schemes 2 and 3.

Compound 5

1-chloro-2-methoxyethane

Calcium carbonate (27.3 g, 273.2 mmol), dimethyl sulfate (23.5 mL, 248.4 mmol), and 2-chloroethanol (16.6 mL, 248.4 mmol) were added in a round bottom flask equipped with a distillation setup, and mixed together to obtain a mixture. The mixture was heated at a temperature ranging from 120° C. to 130° C. until distillation ceased (overnight). Then, the distillate was diluted with ether, washed with a sodium hydroxide aqueous solution (2N). The aqueous layer was extracted again with ether, and then the combined ether layer was dried over $MgSO_4$, and followed by normal distillation (fractions collected at vapor temperature ranging from 88° C. to 90° C.) to obtain a colorless liquid (10.2 g, 43% yield). The spectrum analysis for the colorless liquid obtained by the above procedures is: $^1$H NMR (400 MHz, $CDCl_3$), δ (ppm): 3.62-3.57 (m, 4H), 3.37 (s, 3H); $^{13}$C NMR (100.6 MHz, $CDCl_3$), δ (ppm): 72.5, 58.8, 42.7. The colorless liquid obtained was confirmed to be Compound 5 (1-chloro-2-methoxyethane).

Compound 6

4-methoxy-3-(2-methoxyethoxy)benzaldehyde

Compound 5 (4.1 mL, 44.7 mmol) was added to and mixed with a first mixture including isovanillin (4.0 g, 26.3 mmol), potassium carbonate (6.5 g, 47.3 mmol), and dimethylformamide (DMF, 30 mL) to obtain a second mixture. The second mixture was then stirred at a temperature ranging from 85° C. to 90° C. for 20 hours, cooled to room temperature, and filtered via Büchner funnel, and the residue was washed with EtOAc. The EtOAc filtrate was washed with a sodium hydroxide aqueous solution (2N), water, and brine, and then dried over $MgSO_4$, and concentrated to obtain a yellow oil (5.3 g, 97% yield). The spectrum analysis for the yellow oil obtained by the above procedures is: $^1$H NMR (400 MHz, $CDCl_3$), δ (ppm): 9.83 (s, 1H), 7.47-7.42 (m, 2H), 6.97-6.95 (d, J=8.2 Hz, 1H), 4.23-4.21 (m, 2H), 3.93 (s, 3H), 3.81-3.79 (m, 2H), 3.44 (s, 3H); $^{13}$C NMR (100.6 MHz, $CDCl_3$), δ (ppm): 190.7, 154.9, 148.8, 129.9, 126.8, 110.8, 110.7, 70.6, 68.2, 59.0, 56.0; LRMS-EI$^+$ (m/z): 211 ([M+H]$^+$, 13), 210 ([M]$^+$, 100), 152(67), 123(4), 95(3), 77 (5), 59 (67); HRMS-TOF-ES$^+$ (m/z): [M+H]$^+$ calculated for $C_{11}H_{15}O_4$, 211.0970, found: 211.0971. The yellow oil obtained was confirmed to be Compound 6 (4-methoxy-3-(2-methoxyethoxy)benzaldehyde).

Compound 7

4-methoxy-3-(2-methoxyethoxy)benzonitrile

Sodium formate (1.5 g, 21.9 mmol) and formic acid (23 mL) were added to Compound 6 (2.3 g, 10.9 mmol), followed by stirring for 10 minutes to obtain a clean yellow solution. Next, hydroxylamine hydrochloride (2.3 g, 32.8 mmol) was added to and mixed with the clean yellow solution by stirring at 85° C. for 12 hours, followed by removal of solvent to collect a residue. The residue was then poured into cold water and extracted with EtOAc (75 mL) for three times. EtOAc layers were collected and combined. Thereafter, the combined EtOAc layer was washed with water and brine, dried over $MgSO_4$, and concentrated and dried in high vacuum to obtain a pale orange oil (2.2 g, 97% yield). The spectrum analysis for the pale orange oil obtained in the above procedures is: $^1$H NMR (400 MHz, CDCl$_3$), δ (ppm): 7.22-7.19 (dd, J=2.0, 8.8 Hz, 1H), 7.05 (d, J=1.6 Hz, 1H), 6.82-6.80 (d, J=8.4 Hz, 1H), 4.10-4.07 (m, 2H), 3.83 (s, 3H), 3.72 (m, 2H), 3.37 (s, 3H); $^{13}$C NMR (100.6 MHz, CDCl$_3$), δ (ppm): 153.4, 148.5, 126.8, 119.2, 116.0, 111.5, 103.6, 70.7, 68.7, 59.2, 56.0; LRMS-EI$^+$ (m/z): 208 ([M+H]$^+$, 22), 207 ([M]$^+$, 100), 149(57), 134(22), 117(8), 102(7), 77(4), 59(96); HRMS-TOF-ES$^+$ (m/z): [M+H]$^+$ calculated for C$_{11}$H$_{14}$NO$_3$, 208.0974, found: 208.0976. The pale orange oil obtained was confirmed to be Compound 7 (4-methoxy-3-(2-methoxyethoxy)benzonitrile).

Compound 8

4-methoxy-5-(2-methoxyethoxy)-2-nitrobenzonitrile

A solution including Compound 7 (1.0 g, 4.8 mmol) and AcOH (4 mL) was added dropwise to ice cooled concentrated nitric acid (70%, 10 mL), followed by stirring at room temperature for 12 hours to obtain a mixture. The mixture was then poured into water, followed by filtration and washing with plenty of water to collect a precipitate. The precipitate was dissolved in dichloromethane (DCM), washed with a sodium hydroxide aqueous solution (2N), water, and brine, then dried over MgSO$_4$, and concentrated and dried in high vacuum to obtain a pale yellow powder (1.0 g, 82% yield). The spectrum analysis for the pale yellow powder obtained by the above procedures is: $^1$H NMR (400 MHz, CDCl$_3$), δ (ppm): 7.78 (s, 1H), 7.27 (s, 1H), 4.30-4.27 (m, 2H), 4.00 (s, 3H), 3.83-3.81 (m, 2H), 3.44 (s, 3H); $^{13}$C NMR (100.6 MHz, CDCl$_3$), δ (ppm): 152.9, 152.5, 142.8, 116.8, 115.5, 108.0, 100.6, 70.4, 69.4, 59.3, 56.7; LRMS-EI$^+$ (m/z): 253 ([M+H]$^+$, 16), 252 ([M]$^+$, 100), 207(2), 194(3), 163(3), 136(4), 121(2), 104(4), 59(99); HRMS-TOF-ES$^+$ (m/z): [M+H]$^+$ calculated for C$_{11}$H$_{13}$N$_2$O$_5$, 253.0824, found: 253.0825. The pale yellow powder obtained was confirmed to be Compound 8 (4-methoxy-5-(2-methoxyethoxy)-2-nitrobenzonitrile).

Compound 9

2-amino-4-methoxy-5-(2-methoxyethoxy)benzonitrile

A first solution including Compound 8 (0.5 g, 2.0 mmol) and dichloromethane (10 mL) was added to a second solution including SnCl$_2$ (1.2 g, 5.9 mmol) and concentrated HCl (2 mL) and AcOH (7 mL), followed by stirring at 80° C. for 5 hours to obtain a mixture. Thereafter, the mixture was cooled to an ice bath temperature. The pH value of the mixture was then adjusted to 12 using a sodium hydroxide solution (6N), followed by extraction with dichloromethane (DCM, 50 mL) for three times. DCM layers were collected and combined. The combined DCM layer was then cooled to an ice bath temperature, and then the pH value of the combined DCM layer was adjusted to 1 using a hydrogen chloride aqueous solution (6N), followed by collection of an aqueous layer. The aqueous layer was again washed with DCM, and the pH value of the aqueous layer was adjusted to 12 using a sodium hydroxide solution (6N), followed by extraction with DCM (50 mL) for three times. DCM layers were collected and combined. The combined DCM layer was dried over MgSO$_4$, and concentrated and dried in high vacuum to obtain a brownish solid (350.0 mg, 80% yield). The spectrum analysis for the brownish solid obtained by the above procedures is: $^1$H NMR (400 MHz, CDCl$_3$), δ (ppm): 6.85 (s, 1H), 6.21 (s, 1H), 4.22 (br, 2H), 4.04-4.02 (t, J=4.6 Hz, 2H), 3.81 (s, 3H), 3.72-3.69 (t, J=4.9 Hz, 2H), 3.41 (s, 3H); $^{13}$C NMR (100.6 MHz, CDCl$_3$), δ (ppm): 155.5, 146.7, 140.9, 118.0, 116.9, 99.0, 86.3, 70.9, 69.6, 59.1, 55.8. The brownish solid obtained was confirmed to be Compound 9 (2-amino-4-methoxy-5-(2-methoxyethoxy)benzonitrile).

Comparative Example 2 (CE2)

N-(3-ethynylphenyl)-7-methoxy-6-(2-methoxy-ethoxy) quinazolin-4-amine

Dimethylformamide dimethylacetal (1.3 mL) was added to Compound 9 (0.32 g, 1.4 mmol) followed by reflux for 1.5 hours to obtain a first mixture. The solvent in the first mixture was stripped off completely, followed by drying in high vacuum for 0.5 hour to obtain a brown residue. Thereafter, AcOH (3.2 mL) and 3-ethynylaniline (178.0 μL, 1.5 mmol) were added to the brown residue, and heated at 120° C. for 1.5 hours, followed by cooling to room temperature to obtain a second mixture. The second mixture was poured into water and extracted with EtOAc (25 mL) for three times and with DCM (25 mL) for three times. Organic layers were collected and combined. The combined organic layer was dried over MgSO$_4$, and concentrated and triturated with Methanol (MeOH) to obtain a white solid (250.0 mg, 50% yield). The spectrum analysis for the white solid obtained by the above procedures is: $^1$H NMR (400 MHz, DMSO-d$_6$), δ (ppm): 9.44 (s, 1H), 8.50 (s, 1H), 7.99 (s, 1H), 7.91-7.89 (d, J=8.0 Hz, 1H), 7.83 (s, 1H), 7.41-7.37 (t, J=8.0 Hz, 1H), 7.21-7.19 (m, 2H), 4.28-4.26 (t, J=4.3 Hz, 2H), 4.18 (s, 1H), 3.93 (s, 3H), 3.78-3.76 (t, J=4.4 Hz, 2H), 3.35 (s, 3H); $^{13}$C NMR (100.6 MHz, DMSO-d$_6$), δ (ppm): 156.5, 154.8, 153.2, 148.5, 147.5, 140.2, 129.3, 126.7, 125.1, 123.0, 122.2, 109.3, 107.8, 103.0, 83.9, 80.9, 70.5, 68.5, 58.7, 56.2; LRMS-EI$^+$ (m/z): 350 ([M+H]$^+$, 28), 349 ([M]$^+$, 87), 348 ([M−H]$^+$, 100), 290(80), 275(24), 259(6), 247(8), 230(5), 117(7), 59(10); HRMS-TOF-ES$^+$ (m/z): [M+H]$^+$ calculated for C$_{20}$H$_{20}$N$_3$O$_3$, 350.1505, found: 350.1504. The white solid obtained was confirmed to be a 4-anilinoquinazoline derivative of CE2 (N-(3-ethynylphenyl)-7-methoxy-6-(2-methoxyethoxy) quinazolin-4-amine).

A process for synthesizing a 4-anilinoquinazoline derivative of Comparative Example 3 is shown by Schemes 4 and 5:

[Scheme 4]

Compound 11

[Scheme 5]

Compound 8 where Ac is an acetyl group.

Compound 10

4-hydroxy-5-(2-methoxyethoxy)-2-nitrobenzonitrile

Compound 8 (1.0 g, 3.9 mmol) and aluminum chloride (1.6 g, 11.9 mmol) were loaded into a seal tube, and then dichloromethane (DCM, 20 mL) was further loaded into the seal tube, followed by stirring at 70° C. for 2 hours. Thereafter, the mixture in the seal tube was cooled in an ice bath, and then quenched with a hydrogen chloride solution (1N, 100 mL), followed by extracted with DCM (50 mL) for five times. DCM layers were collected and combined. The pH value of the combined DCM layer was adjusted to 10 using a sodium hydroxide aqueous solution (2N), followed by collection of an aqueous layer. The aqueous layer was washed again with DCM, and cooled to an ice bath temperature. Next, the pH value of the aqueous layer was adjusted to 2 using a hydrogen chloride solution (6N), followed by extracted with DCM (50 mL) for five times. DCM layers were collected and combined. The combined DCM layer was dried over MgSO$_4$, and concentrated to obtain a yellow solid (710.0 mg, 75% yield). The spectrum analysis for the yellow solid obtained by the above procedures is: $^1$H NMR (400 MHz, DMSO-d$_6$), δ (ppm): 11.31 (s, 1H), 7.71 (s, 1H), 7.64 (s, 1H), 4.30 (s, 2H), 3.69 (s, 2H), 3.30 (s, 3H); $^{13}$C NMR (100.6 MHz, DMSO-d$_6$), δ (ppm): 152.2, 151.3, 142.5, 118.4, 116.5, 112.5, 98.1, 70.4, 69.3, 58.6; LRMS-EI$^+$ (m/z): 239 ([M+H]$^+$, 28), 238 ([M]$^+$, 98), 206(85), 194(7), 176(9), 132(4), 104(6), 88(3), 76(5), 59 (100); HRMS-TOF-ES$^+$ (m/z): [M]$^+$ calculated for C$_{10}$H$_{10}$N$_2$O$_5$, 238.0590, found: 238.0590. The yellow solid obtained was confirmed to be Compound 10 (4-hydroxy-5-(2-methoxyethoxy)-2-nitrobenzonitrile).

Compound 11

2-bromoethyl acetate

To a solution of 2-bromoethanol (2.0 g, 16.0 mmol) and 4-(N,N-dimethylamino)pyridine (2.6 g, 21.6 mmol) in DCM (20 mL), acetic anhydride (2.0 mL, 20.8 mmol) was added dropwise at ice bath temperature under argon atmosphere to obtain a mixture. The mixture was then stirred for 15 hours at room temperature, and poured into water. An aqueous layer was collected and extracted again with DCM. A DCM layer was collected and concentrated to obtain a yellow liquid (2.2 g, 82% yield). The spectrum analysis for the yellow liquid obtained by the above procedures is: $^1$H NMR (400 MHz, CDCl$_3$), δ (ppm): 4.35-4.31 (td, J=1.6, 6.4 Hz, 2H), 3.49-3.45 (td, J=1.6, 6.4 Hz, 2H), 2.06-2.05 (d, J=1.6 Hz, 3H); $^{13}$C NMR (100.6 MHz, CDCl3), δ (ppm): 170.4, 63.7, 28.6, 20.7. The yellow liquid obtained was confirmed to be Compound 11 (2-bromoethyl acetate).

Compound 12

2-[4-cyano-2-(2-methoxyethoxy)-5-nitrophenoxy] ethyl acetate

Compound 11 (1.7 g, 10.0 mmol) was added to slurry of Compound 10 (1.6 g, 6.7 mmol) and potassium carbonate (1.2 g, 8.7 mmol) in DMF (16 mL) to obtain a mixture. The mixture was stirred at 85° C. for 15 hours, cooled to room temperature, and filtered via Büchner funnel, and the residue was washed with EtOAc. The filtrate was then washed with a saturated Sodium bicarbonate solution, water, and brine, dried over MgSO$_4$, and concentrated to obtain a crude product. Thereafter, the crude product was purified by column chromatography (70-230 mesh silica gel, 40-60% EtOAc/Hexane) to obtain a pale yellow solid (1.9 g, 88% yield). The spectrum analysis for the pale yellow solid obtained by the above procedures is: $^1$H NMR (400 MH$_z$, CDCl$_3$), δ (ppm): 7.83 (s, 1H), 7.29 (s, 1H), 4.51-4.48 (t, J=4.4 Hz, 2H), 4.37-4.35 (t, J=5.0 Hz, 2H), 4.29-4.27 (t, J=4.4 Hz, 2H), 3.82-3.80 (t, J=3.4 Hz, 2H), 3.45 (s, 3H), 2.10 (s, 3H); $^{13}$C NMR (100.6 MHz, CDCl$_3$), δ (ppm): 170.7, 153.2, 151.4, 142.6, 117.5, 115.4, 109.7, 101.2, 70.4, 69.7, 67.7, 62.0, 59.4, 20.7. LRMS-EI$^+$ (m/z): 325 ([M+H]$^+$, 7), 32 ([M]$^+$, 18), 281(2), 206(6), 191(6), 145(5), 87(100), 59(61); HRMS-TOF-ES$^+$ (m/z): [M+Na]$^+$ calculated for C$_{14}$H$_{16}$N$_2$O$_7$Na, 347.0855, found: 347.0857. The pale yellow solid obtained was confirmed to be Compound 12 (2-[4-cyano-2-(2-methoxyethoxy)-5-nitrophenoxy]ethyl acetate).

Compound 13

2-[5-amino-4-carbamoyl-2-(2-methoxyethoxy) phenoxy]ethyl acetate

Fe (1.2 g, 21.5 mmol) was added to a solution of Compound 12 (2.0 g, 6.2 mmol) and ammonium chloride (1.7 g, 30.8 mmol) in Methanol (MeOH) (25 mL) and water (50 mL), followed by refluxed for 1 hour to obtain a hot mixture. The hot mixture was filtered via celite bed after the celite bed had been washed with hot MeOH to collect a filtrate. The filtrate was then evaporated and the residue was taken up in a mixture of a saturated sodium bicarbonate aqueous solution and EtOAc. An aqueous layer was collected and extracted again with EtOAc (50 mL) for four times. EtOAc layers are collected and combined. The combined EtOAc layer was dried over $MgSO_4$ and concentrated to obtain a crude product. Then, the crude product was purified by column chromatography (230-400 mesh silica gel, 2-5% MeOH/DCM) to obtain a brown gummy oil (1.6 g, 83% yield). The spectrum analysis for the brown gummy oil obtained by the above procedures is: $^1H$ NMR (400 MHz, $CDCl_3$), δ (ppm): 7.04 (s, 1H), 6.13 (s, 1H), 5.96 (br, 2H), 5.66 (br, 2H), 4.41-4.38 (t, J=4.6 Hz, 2H), 4.13-4.11 (t, J=4.7 Hz, 2H), 4.03-4.01 (t, J=4.3 Hz, 2H), 3.65-3.63 (t, J=4.4 Hz, 2H), 3.39 (s, 3H), 2.05 (s, 3H); $^{13}C$ NMR (100.6 MHz, $CDCl_3$), δ (ppm): 171.1, 170.9, 154.1, 146.9, 139.1, 118.0, 106.0, 101.8, 71.3, 71.0, 66.4, 62.4, 59.0, 20.8. LRMS-EI$^+$ (m/z): 313 ([M+H]$^+$, 11), 312 ([M]$^+$, 67), 226(100), 167(24), 150(9), 87(100), 59(9); HRMS-TOF-ES$^+$ (m/z): [M+Na]$^+$ calculated for $C_{14}H_{20}N_2O_6Na$, 335.1219, found: 335.1219. The brown gummy oil obtained was confirmed to be Compound 13 (2-[5-amino-4-carbamoyl-2-(2-methoxyethoxy) phenoxy]ethyl acetate).

Compound 14

2-{[6-(2-methoxyethoxy)-4-oxo-3,4-dihydroquinazolin-7-yl]oxy}ethyl acetate

Compound 13 (167.0 mg, 0.56 mmol) and dimethylformamide dimethylacetal (0.8 mL) were mixed together and refluxed at 120° C. for 1.5 hours under argon atmosphere to obtain a first mixture. Then, the solvent in the first mixture was stripped off and dried under high vacuum for 0.5 hour to obtain a brown residue. AcOH (1.7 mL) was added to the brown residue, heated at 130° C. for 2.5 hours, stirred at room temperature for 10 hours, and then poured into water to obtain a second mixture. The pH value of the second mixture was adjusted to 10 using a sodium hydroxide aqueous solution (2N), followed by extracted with DCM (20 mL) for four times. DCM layers were collected and combined. The combined DCM layer was dried over $MgSO_4$ and concentrated and dried under high vacuum to obtain a yellow solid (144.0 mg, 79% yield). The spectrum analysis for the yellow solid obtained by the above procedures is: $^1H$ NMR (400 MHz, DMSO-$d_6$), δ (ppm): 12.09 (b, 1H), 7.98 (s, 1H), 7.46 (s, 1H), 7.17 (s, 1H), 4.39-4.34 (m, 4H), 4.20-4.18 (t, J=4.1 Hz, 2H), 3.71-3.69 (t, J=4.4 Hz, 2H), 3.33 (s, 3H), 2.04 (s, 3H); $^{13}C$ NMR (100.6 MHz, $CDCl_3$), δ (ppm): 170.9, 162.3, 154.4, 148.7, 145.3, 142.7, 115.9, 109.4, 106.8, 70.6, 68.7, 66.8, 62.2, 59.3, 20.8; LRMS-EI$^+$ (m/z): 323 ([M+H]$^+$, 20), 322 ([M]$^+$, 86), 236(8), 22(13), 204(17), 189(16), 178(30), 148(4), 87(100), 59(43); HRMS-TOF-ES$^+$ (m/z): [M+H]$^+$ calculated for $C_{15}H_{19}N_2O_6$, 323.1243, found: 323.1245. The yellow solid obtained was confirmed to be Compound 14 (2-{[6-(2-methoxyethoxy)-4-oxo-3,4-dihydroquinazolin-7-yl]oxy}ethyl acetate).

Comparative Example 3 (CE3)

2-{[4-((3-ethynylphenyl)amino)-6-(2-methoxyethoxy) quinazolin-7-yl]oxy}ethyl acetate Thiony chloride (6 mL) was added to Compound 14 (950.0 mg, 2.9 mmol), followed by addition DMF (0.1 mL) in a catalytic amount to obtain a first mixture. The first mixture was heated at 120° C. for 2 hours, and the solvent in the first mixture was removed by evaporation under high vacuum using rotavapor for drying the first mixture for 3 hours to obtain a brown residue. DMF (10 mL) was added to the brown residue, and then 3-ethynylaniline 10 (0.4 mL, 3.2 mmol) was further added for stirring for at 120° C. for 2 hours, followed by cooling to room temperature to obtain a second mixture. Thereafter, water was poured into the second mixture, followed by filtration to collect a precipitate. The precipitate was washed with plenty of water to collect a brownish yellow crude product. Then, the brownish yellow crude product was dissolved in a solvent mixture of DCM and MeOH, and evaporated using rotavapor and dried under high vacuum to obtain a brownish yellow solid product (990.0 mg, 80% yield). The spectrum analysis for the brownish yellow solid product obtained by the above procedures is: $^1H$ NMR (400 MHz, DMSO-$d_6$), δ (ppm): 9.49 (s, 1H), 8.50 (s, 1H), 7.99 (s, 1H), 7.91-7.87 (m, 2H), 7.42-7.38 (t, J=7.9 Hz, 1H), 7.25 (s, 1H), 7.22-7.20 (d, J=7.6 Hz, 1H), 4.40-4.39 (m, 4H), 4.30-4.28 (t, J=4.4 Hz, 1H), 4.21 (s, 1H), 3.79-3.77 (t, J=4.6 Hz, 1H), 3.37 (s, 3H), 2.05 (s, 3H); $^{13}C$ NMR (100.6 MHz, DMSO-$d_6$), δ(ppm): 170.7, 156.5, 153.7, 153.2, 148.5, 147.4, 140.2, 129.3, 126.8, 125.2, 109.5, 108.9, 103.9, 83.9, 81.0, 70.5, 69.0, 67.1, 62.5, 58.9, 21.1; LRMS-EI$^+$ (m/z): 422 ([M+H]$^+$, 26), 421 ([M]$^+$, 100), 420 ([M−H]$^+$, 75), 334(74), 302(15), 290(11), 276 (47), 116(5), 87(83), 59(10); HRMS-TOF-ES$^+$ (m/z): [M+H]$^+$ calculated for $C_{23}H_{24}N_3O_5$, 422.1716, found: 422.1714. The brownish yellow solid product obtained was confirmed to be a 4-anilinoquinazoline derivative of CE3 (2-{[4-((3-ethynylphenyl)amino)-6-(2-methoxyethoxy) quinazolin-7-yl]oxy}ethyl acetate). The spectrum analysis for the brown residue obtained in the above procedures is: $^1H$ NMR (400 MHz, $CDCl_3$), δ (ppm): 9.04 (s, 1H), 8.22 (s, 1H), 7.58 (s, 1H), 4.55 (s, br, 4H), 4.40 (s, br, 2H), 3.89 (s, br, 2H), 3.48 (s, 3H), 2.11 (s, 3H). The brown residue obtained was confirmed to be Intermediate compound 2 shown in Scheme 5.

A process for synthesizing 4-anilinoquinazoline derivatives of Example 1 and Comparative Examples 4 to 6 is shown by Scheme 6.

[Scheme 6]

Comparative Example 3

-continued

Comparative Example 4

Comparative Example 5

Example 1

Comparative Example 6 where Ac is an acetyl group and Ms is a methanesulfonyl group.

Comparative Example 4 (CE4)

2-{[4-((3-ethynylphenyl)amino)-6-(2-methoxy-ethoxy) quinazolin-7-yl]oxy}ethanol

The 4-anilinoquinazoline derivative of CE3 (750.0 mg, 1.8 mmol) was dissolved in MeOH (20 mL), and then a potassium hydroxide aqueous solution (5M, 1.75 mL) was further added for stirring at room temperature for 1.5 hours, followed by evaporated using rotavapor for removal of the solvent to collect a dried product. Water (50 mL) was added to and well-mixed with the dried product for stirring for 15 minutes, followed by decanting the water. The water addition, mixing, and decanting were repeated twice to obtain a gummy mass. Then, for complete removal of solvent, the gummy mass was dried azeotropically by rotavapor three times with acetonitrile to obtain a crude product. The crude product was dried under high vacuum to obtain a yellow solid (650.0 mg, 97% yield). The spectrum analysis for the yellow solid obtained by the above procedures is: $^1$H NMR (400 MHz, CDCl$_3$), δ (ppm): 8.76 (br, 1H), 8.48 (s, 1H), 7.82 (s, 1H), 7.74-7.72 (d, J=7.8 Hz, 1H), 7.48 (s, 1H), 7.22-7.18 (t, J=7.7 Hz, 1H, 7.13-7.12 (d, J=7.4 Hz, 1H), 6.98 (s, 1H), 4.56 (br, 1H), 4.07-4.03 (m, 4H), 3.89 (s, 2H), 3.60 (s, 2H), 3.25 (s, 3H), 3.03 (s, 1H); $^{13}$C NMR (100.6 MHz, DMSO-d$_6$), δ (ppm): 156.5, 154.3, 153.2, 148.6, 147.4, 140.3, 129.2, 126.2, 125.2, 123.0, 122.1, 109.3, 108.5, 103.6, 84.0, 80.8, 70.8, 70.5, 68.7, 59.7, 58.8; LRMS-EI$^+$ (m/z): 380 ([M+H]$^+$, 30), 379 ([M]$^+$, 93), 378 ([M−H]$^+$, 100), 334(12), 320(47), 290(15), 276(46), 259(4), 230(5), 149(6), 59(10); HRMS-TOF-ES$^+$ (m/z): [M+H]$^+$ calculated for C$_{21}$H$_{22}$N$_3$O$_4$, 380.1610, found: 380.1613. The yellow solid obtained was confirmed to be a 4-anilinoquinazoline derivative of CE4 (2-{[4-((3-ethynylphenyl)amino)-6-(2-methoxyethoxy) quinazolin-7-yl]oxy}ethanol).

Comparative Example 5 (CE5)

2-{[4-((3-ethynylphenyl)amino)-6-(2-methoxy-ethoxy) quinazolin-7-yl]oxy}ethyl methanesulfonate Methanesulfonyl chloride (30.0 μL, 0.39 mmol) was added to a solution of the 4-anilinoquinazoline derivative of CE4 (100.0 mg, 0.26 mmol) and 4-dimethylaminopyridine (DMAP, catalytic, 10.0 mg) in pyridine (2.5 mL) at an ice bath temperature under argon atmosphere to obtain a mixture. The mixture was stirred at room temperature for 20 hours, and was subsequently quenched with a saturated sodium bicarbonate solution, followed by extracted with EtOAc (15 mL) for five times. EtOAc layers were collected and combined. The combined EtOAc layer was dried over MgSO$_4$, filtered, concentrated, and purified by column chromatography (230-400 mesh, EtOAc, then 2% MeOH in EtOAc) to obtain a pale yellow solid (102.0 mg, 84% yield). The spectrum analysis for the pale yellow solid obtained by the above procedures is: $^1$H NMR (400 MHz, CDCl$_3$), δ (ppm): 8.58 (s, 1H), 7.89 (br, 1H), 7.81 (s, 1H), 7.73-7.71 (d, J=8.2 Hz, 1H), 7.31-7.27 (t, J=7.6 Hz, 1H), 7.22-7.19 (m, 2H), 7.03 (s, 1H), 4.58-4.56 (t, J=3.9 Hz, 2H), 4.18-4.16 (t, J=4.0 Hz, 2H), 4.14-4.12 (t, J=4.3 Hz, 2H), 3.71-3.69 (t, J=4.4 Hz, 2H), 3.38 (s, 3H), 3.14 (s, 3H), 3.08 (s, 1H); $^{13}$C NMR (100.6 MHz, CDCl$_3$), δ (ppm): 156.3, 153.6, 153.2, 148.5, 147.0, 138.8, 129.0, 127.8, 125.1, 122.7, 122.5, 109.5, 108.4, 101.9, 83.3, 77.6, 70.7, 68.5, 68.1, 66.3, 59.1, 37.7; LRMS-EI$^+$ (m/z): 458 ([M+H]$^+$, 7), 457 ([M]$^+$, 26), 456 ([M−H]$^+$, 25), 398(44), 338(36), 302(29), 276(28), 125(24), 111(31), 97(33), 85(29), 71(29), 59(16); HRMS-TOF-ES$^+$ (m/z): [M+H]$^+$ calculated for C$_{22}$H$_{24}$N$_3$O$_6$S, 458.1386, found: 458.1388. The pale yellow solid obtained was confirmed to be a 4-anilinoquinazoline derivative of CE5 (2-{[4-((3-ethynylphenyl)amino)-6-(2-methoxyethoxy)quinazolin-7-yl]oxy}ethyl methanesulfonate).

Example 1 (E1)

N-(3-ethynylphenyl)-7-(2-iodoethoxy)-6-(2-methoxyethoxy)quinazolin-4-amine

The 4-anilinoquinazoline derivative of CE5 (50.0 mg, 0.1 mmol) and sodium iodide (164.0 mg, 1.0 mmol) were loaded into a seal tube, and then acetone was further loaded into the seal tube, followed by heating at 80° C. for 24 hours to obtain a mixture. The mixture was then filtered to collect a residue. Thereafter, the residue was washed with EtOAc to collect filtrates. The combined filtrate was concentrated and purified by column chromatography (230-400 mesh, 100% EtOAc) to obtain a yellow solid (39.0 mg, 73% yield). The spectrum analysis for the yellow solid obtained by the above procedures is: 1H NMR (400 MHz, CDCl$_3$), δ (ppm): 8.64 (s, 1H), 8.09 (s, 1H), 7.85 (s, 1H), 7.76-7.74 (d, J=8.0 Hz, 1H), 7.37-7.34 (t, J=7.6 Hz, 1H), 7.29-7.27 (d, J=8.0 Hz, 1H), 7.23 (s, 1H), 7.19 (s, 1H), 4.40-4.36 (t, J=6.8 Hz, 2H), 4.32-4.30 (t, J=4.6 Hz, 2H), 3.87-3.85 (t, J=4.7 Hz, 2H), 3.52-3.48 (m, 5H), 3.10 (s, 1H); $^{13}$C NMR (100.6 MHz, CDCl$_3$), δ (ppm): 156.1, 153.7, 153.7, 148.8, 147.4, 138.6, 129.0, 127.9, 124.9, 122.9, 122.2, 109.3, 109.1, 103.2, 83.3, 77.5, 71.0, 69.7, 69.2, 59.5, 29.7; LRMS-EI$^+$ (m/z): 490 ([M+H]$^+$, 24), 489 ([M]$^+$, 100), 430(9), 302(17), 288(6), 275(13), 258(8), 246(7), 230(7), 59 (6); HRMS-TOF-ES$^+$ (m/z): [M+H]$^+$ calculated for $C_{21}H_{21}N_3O_3I$, 490.0628, found: 490.0631. The yellow solid obtained was confirmed to be a 4-anilinoquinazoline derivative of E1 (N-(3-ethynylphenyl)-7-(2-iodoethoxy)-6-(2-methoxyethoxy)quinazolin-4-amine).

Comparative Example 6 (CE6)

7-(2-aminoethoxy)-N-(3-ethynylphenyl)-6-(2-methoxyethoxy) quinazolin-4-amine

The 4-anilinoquinazoline derivative of E1 (20.0 mg) was loaded into a seal tube, and then methanolic ammonia (30%, 3.0 mL) was further loaded into the seal tube for stirring at room temperature for 5 hours, followed by stirring at 85° C. for 6 hours to obtain a mixture. Thereafter, all solvents in the mixture were evaporated using rotavapor for drying dried under high vacuum to obtain a solid product (14.0 mg, 91% yield). The spectrum analysis for the solid product obtained by the above procedures is: $^1$H NMR (400 MHz, MeOD-d$_4$), δ (ppm): 8.43 (s, 1H), 7.94 (s, 1H), 7.79 (s, 1H), 7.77 (s, 1H), 7.39-7.35 (t, J=7.9 Hz, 1H), 7.27-7.25 (d, J=7.6 Hz, 1H), 7.16 (s, 1H), 4.39-4.37 (t, J=4.2 Hz, 4H), 3.91-3.89 (t, J=4.3 Hz, 2H), 3.53 (s, 1H), 3.50-3.46 (m, 5H); $^{13}$C NMR (100.6 MHz, MeOD-d$_4$), δ (ppm): 157.0, 153.3, 152.7, 148.6, 145.9, 139.0, 128.5, 127.4, 125.7, 122.9, 122.7, 109.8, 107.7, 102.8, 82.8, 77.4, 70.3, 68.1, 65.4, 57.9, 38.7; LRMS-EI$^+$ (m/z): 379 ([M+H]$^+$, 14), 378 ([M]$^+$, 45), 377 ([M–H]$^+$, 24), 349(29), 348(93), 335(54), 334(100), 318(36), 304(26), 290(37), 276 (68), 260(18), 59(11); HRMS-TOF-ES$^+$ (m/z): [M+H]$^+$ calculated for $C_{21}H_{23}N_4O_3$, 379.1770, found: 379.1771. The solid product obtained was confirmed to be a 4-anilinoquinazoline derivative of CE6 (7-(2-aminoethoxy)-N-(3-ethynylphenyl)-6-(2-methoxyethoxy) quinazolin-4-amine).

Figure 4:
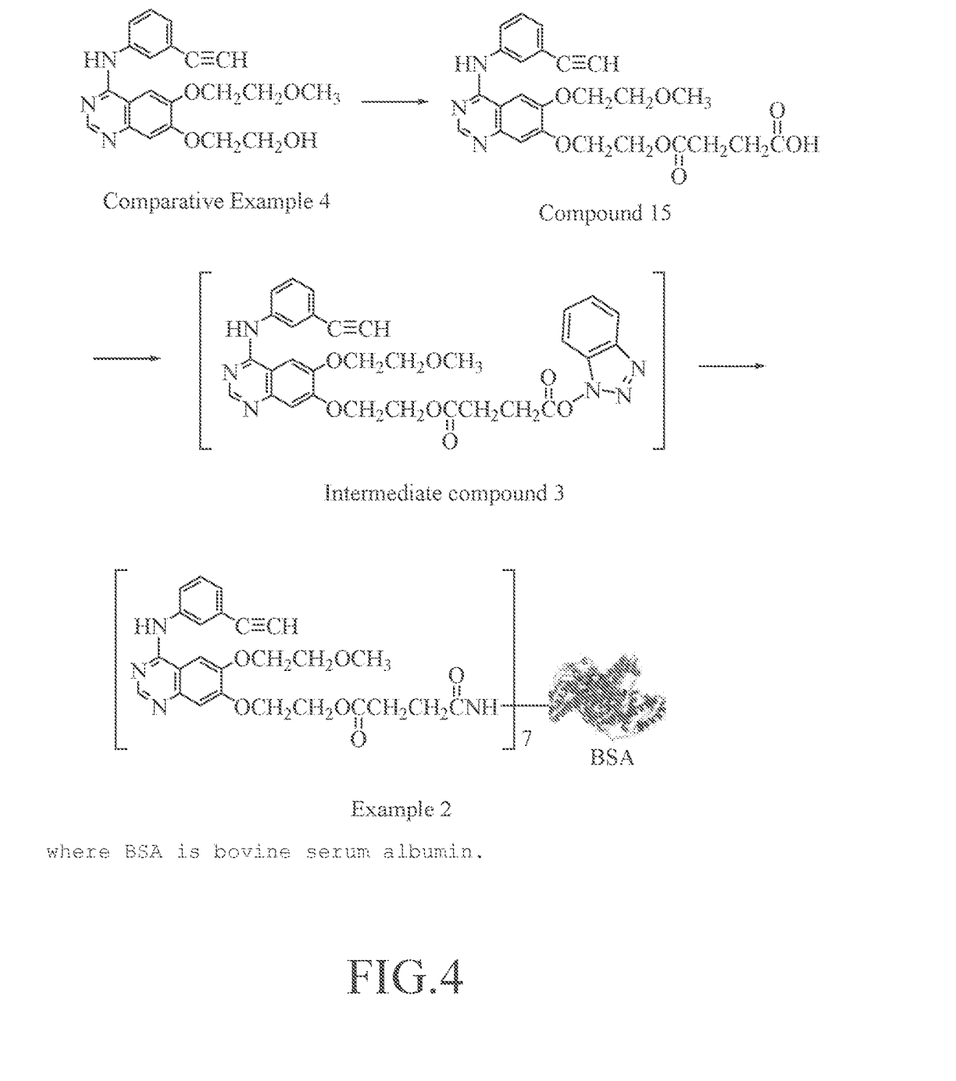
FIG. 4 shows a synchronization scheme for a 4-anilinoquinazoline derivative of Example 2.

A process for synthesizing a 4-anilinoquinazoline derivative of Example 2 is shown by a synchronization scheme in FIG. 4.

Example 2

Compound 15

4-{2-[(4-((3-ethynylphenyl)amino)-6-(2-methoxyethoxy)quinazolin-7-yl)oxy]ethoxy}-4-oxobutanoic acid, monosuccinate Pyridine (1 mL) was added to a solid mixture of the 4-anilinoquinazoline derivative of CE4 (50.0 mg, 0.13 mmol) and succinic anhydride (13.1 mg, 0.13 mmol) to obtain a clear solution. 4-dimethylaminopyridine (DMAP, catalytic, 3.0 mg) was added to the clear solution for stirring at room temperature for 30 hours until the reaction finished (monitored by TLC). After the solvent was evaporated, a solid crude product (62.3 mg, 99% yield) was obtained. The spectrum analysis for the solid crude product obtained by the above procedures is: 1H NMR δ (ppm): 2.67-2.64 (m); LRMS-EI$^+$ (m/z): 479 ([M]$^+$, 25), 379(100), 378(100), 334 (22), 320(99), 302(18), 290(27), 276(89), 259(9), 248(7), 230(8), 59(18); HRMS-TOF-ES$^+$ (m/z): [M+H]$^+$ calculated for $C_{25}H_{26}N_3O_7$, 480.1771, found: 480.1767. The solid crude product obtained was confirmed to be Compound 15 (4-{2-[(4-((3-ethynylphenyl)amino)-6-(2-methoxyethoxy) quinazolin-7-yl)oxy]ethoxy}-4-oxo butanoic acid, monosuccinate).

Example 2

To a 10 mL round bottom flask in which Compound 15 (27.0 mg, 5.6×10$^{-5}$ mmol) and Na CO$_3$ (6.0 mg, 5.6×10$^{-5}$ mmol) were contained, water (1 mL) was added for stirring at room temperature for 10 minutes to obtain a first solution. To the first solution, a phosphate buffer saline (4 mL, pH 7.54) was added, and 1-ethyl-3-(3-dimethylaminopropyl) carbodiimide hydrochloride (EDC.HCl, 10.8 mg, 5.6×10$^{-5}$ mmol) and hydroxybenzotriazole (HOBt, 8.6 mg, 5.6×10$^{-5}$ mmol) were subsequently added, followed by stirring at room temperature for 1.5 hours to obtain a second solution containing Intermediate compound 3 shown in Scheme 7. Then, BSA (50.0 mg, 0.7×10$^6$ mmol) was added to the second solution, followed by stirring at room temperature for 24 hours to obtain a reaction mixture. The reaction mixture was then purified via dialysis (Spectra/Pro 7 dialysis membrane, MWCO, 25000) against deionized distilled water for 2 days. The purified reaction mixture was then lyophilized to obtain a white flake (54.0 mg). The MALDI mass spectrometry for the white flask obtained by the above procedures is: MALDI-MS (CCA matrix, (m/z)): 69679.817 (~7 molecules of monosuccinate attached into BSA). The white flake obtained was confirmed to be a 4-anilinoquinazoline derivative of E2 shown in Scheme 7.

Cell Lines and Cell Culture

A549 cell (ATCC number: CCL-185) was a non-small cell lung carcinoma cell line, expressing wild type EGFR and K-RAS mutation (G12S). H1975 cell (ATCC number: CRL-5908) was a non-small cell lung carcinoma cell line expressing EGFR L858R/T790M mutation. A549 and H1975 cells were cultured in a complete medium at 37° C., 5% CO2 within a humidified incubator (310/Thermo, Forma Scientific, Inc., Marietta, Ohio). The complete medium was RPMI-1640 medium (Gibco, Life Technologies, Grand Island, N.Y., USA) supplemented with 10% fetal bovine serum (FBS), penicillin (100 units/mL), streptomycin (100 μg/mL), and sodium bicarbonate.

Cell Viability Assay (MTT Assay)

Figure 1:
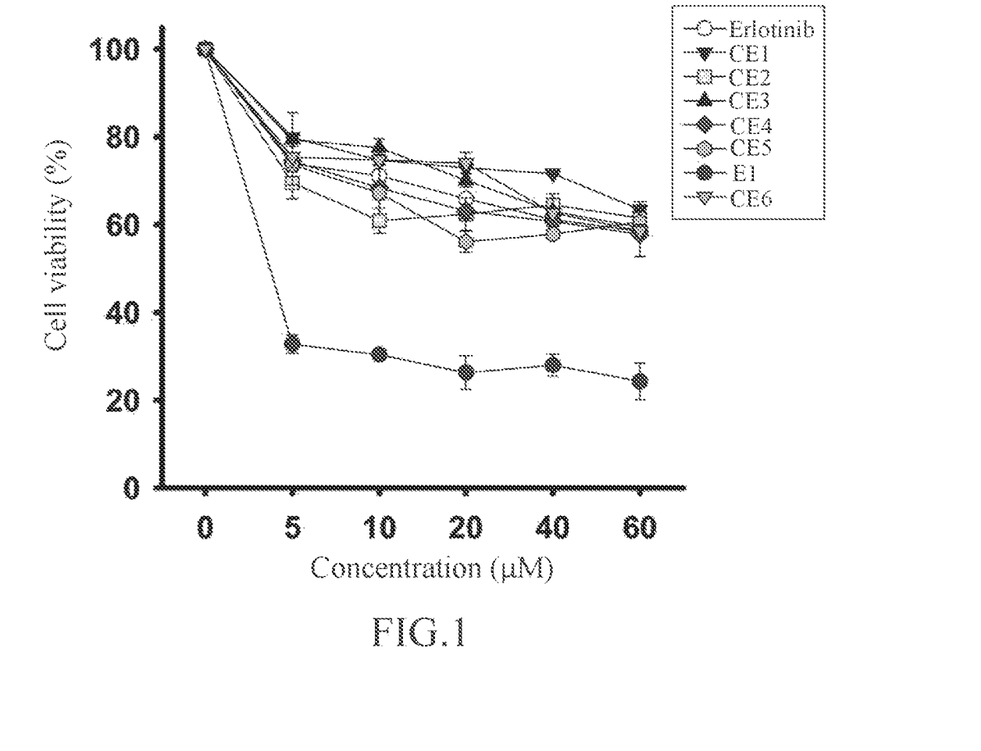
FIG. 1 shows a set of survival curves of A549 cells treated with various 4-anilinoquinazoline derivatives.
Figure 2:
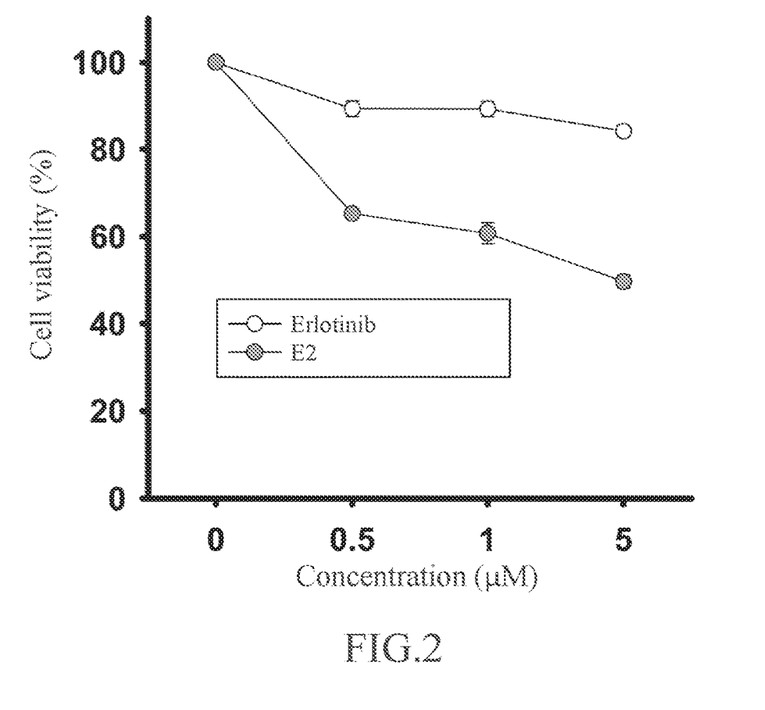
FIG. 2 shows two survival curves of A549 cells which were respectively treated by a commercial available Erlotinib and a 4-anilinoquinazoline derivative of Example 2.
Figure 3:
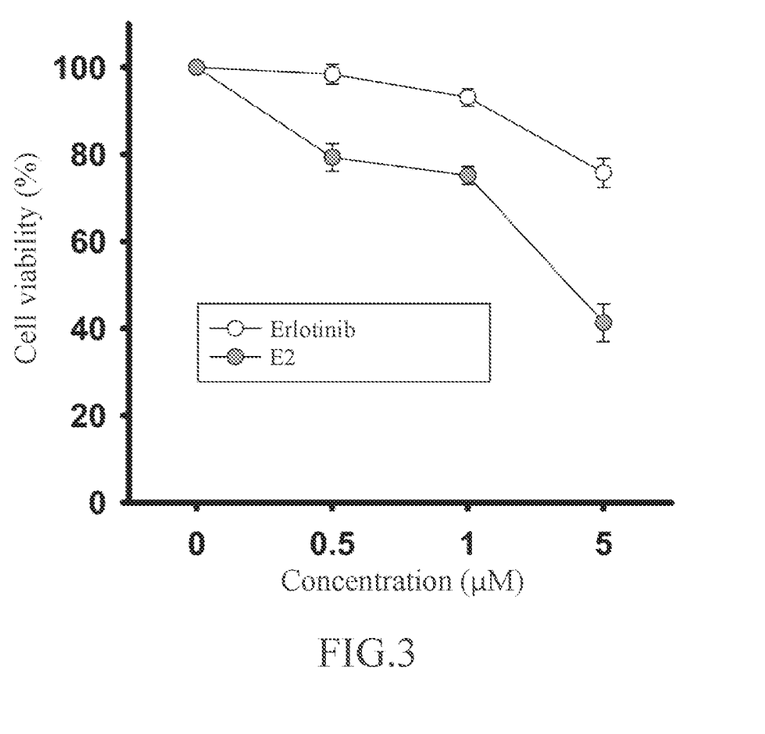
FIG. 3 shows two survival curves of H1975 cells which were respectively treated by the commercial available Erlotinib and the 4-anilinoquinazoline derivative of Example 2.

The cells were plated in 96-well plates at a density of 1×10$^4$ cells/well for 16-20 hours. Thereafter, the cells in each well were treated by 0.1 mL of a treating agent for 24 hours. The treating agents for the wells were different in treating chemicals and their concentrations. The treating chemicals were Erlotinib, Erlotinib analogues (CE 1 to 6 and E1), and BSA-conjugated Erlotinib Analogue (E2). Next, the cells were washed with phosphate-buffered saline (PBS) and were further cultured with fresh complete medium for 2 days. Subsequently, the cells were incubated with 0.5 mg/ml of 3-(4,5-dimethylthiazol-2-yl)-2,5-diphenyltetrazolium bromide (MTT) in fresh complete medium for 4 hours, followed by removal of the medium and addition of dimethyl sulfoxide (DMSO, 0.1 mL) to thereby allow viable cells to convert yellow-colored MTT to dark-blue formazan crystal. The absorbance of the reduced MTT (formazan) was read on a microplate reader (VERSAmax, Molecular Devices Inc., CA) at 565 nm. Total pigmentation was calculated and normalized to cell viability values. Tables 1 and 2, and FIGS. 1 and 2 show cell viability values for A549 cell using different treating chemicals in different concentrations. Table 3 and FIG. 3 show cell viability values for H1975 cell using two treating chemicals in different concentrations.

TABLE 1

| | | Conc. of treating chemical (µM) | | | | | |
|---|---|---|---|---|---|---|---|
| | | 0 | 5 | 10 | 20 | 40 | 60 |
| | | Cell viability (%) | | | | | |
| Treating chemical | Erlotinib | 100% | 73.8% ± 2.8 | 71.7% ± 3.2 | 65.9% ± 2.1 | 61.2% ± 3.5 | 58.5% ± 3.8 |
| | CE1 | 100% | 79.9% ± 1.3 | 74.7% ± 1.5 | 73.0% ± 2.2 | 71.6% ± 0.4 | 63.4% ± 1.5 |
| | CE2 | 100% | 69.5% ± 2.5 | 60.9% ± 2.4 | 62.4% ± 2.5 | 64.5% ± 1.7 | 61.6% ± 2.8 |
| | CE3 | 100% | 79.3% ± 5.3 | 77.5% ± 1.5 | 70.1% ± 1.0 | 63.0% ± 2.2 | 59.5% ± 1.3 |
| | CE4 | 100% | 74.5% ± 4.7 | 68.4% ± 5.1 | 63.1% ± 1.2 | 60.7% ± 2.4 | 57.8% ± 3.8 |
| | CE5 | 100% | 73.7% ± 1.2 | 67.2% ± 1.3 | 56.1% ± 1.8 | 57.9% ± 0.8 | 60.7% ± 0.8 |
| | CE6 | 100% | 75.4% ± 1.7 | 74.8% ± 0.9 | 74.1% ± 1.6 | 62.7% ± 0.8 | 58.6% ± 1.1 |
| | E1 | 100% | 32.8% ± 1.5 | 30.3% ± 0.8 | 26.3% ± 3.0 | 28.0% ± 2.1 | 24.3% ± 3.6 |

TABLE 2

| | | Conc. of treating chemical (µM) | | | |
|---|---|---|---|---|---|
| | | 0 | 0.5 | 1 | 5 |
| | | Cell viability (%) | | | |
| Treating chemical | Erlotinib | 100% | 89.3% ± 2.2 | 89.3% ± 2.3 | 84.2% ± 1.7 |
| | E2 | 100% | 65.3% ± 0.7 | 60.8% ± 1.8 | 49.8% ± 1.0 |

It can be found in Tables 1 and 2, and FIGS. 1 and 2 that in comparison with the commercial available drug (Erlotinib), A549 cells had significantly lower cell viability when treating with 4-anilinoquinazoline derivatives of E1 and E2.

TABLE 3

| | | Conc. of treating chemical (µM) | | | |
|---|---|---|---|---|---|
| | | 0 | 0.5 | 1 | 5 |
| | | Cell viability (%) | | | |
| Treating chemical | Erlotinib | 100% | 98.4% ± 2.7 | 93.1% ± 2.5 | 75.8% ± 4.5 |
| | E2 | 100% | 79.3% ± 2.2 | 75.1% ± 1.4 | 41.4% ± 3.3 |

It can be found in Table 3 and FIG. 3 that in comparison with the commercial available drug (Erlotinib), H1975 cells had significantly lower cell viability when treating with 4-anilinoquinazoline derivative of E2.

As set forth before, A549 cell (ATCC number: CCL-185) is a non-small cell lung carcinoma cell line, expressing wild type EGFR and K-RAS mutation, while H1975 cell (ATCC number: CRL-5908) is a non-small cell lung carcinoma cell line, expressing EGFR L858R/T790M mutation. Thus, it can be concluded that the 4-anilinoquinazoline derivatives of E1 and E2 would be useful for preventing, treating, or ameliorating one or more symptoms of a malignant tumor, such as non-small-cell lung carcinoma (NSCLC), associated with EGFR mutation and/or K-RAS mutation.

While the disclosure has been described in connection with what is (are) considered the exemplary embodiment(s), it is understood that this disclosure is not limited to the disclosed embodiment (s) but is intended to cover various arrangements included within the spirit and scope of the broadest interpretation so as to encompass all such modifications and equivalent arrangements.

What is claimed is:

1. A pharmaceutical composition for treating or ameliorating one or more symptoms of non-small-cell lung carcinoma, the pharmaceutical composition comprising a 4-anilinoquinazoline derivative having formula (I):

wherein
A is iodine when m is 1 and n is zero, or
A is albumin when m is an integral ranging from 1 to 7 and n is 1.

2. The pharmaceutical composition according to claim 1, wherein A is serum albumin.

3. The pharmaceutical composition according to claim 2, wherein A is bovine serum albumin.

4. The pharmaceutical composition according to claim 1, wherein the 4-anilinoquinazoline derivative is represented by formula (II):

5. The pharmaceutical composition according to claim 3, wherein the 4-anilinoquinazoline derivative is represented by formula (III):

wherein m is an integral ranging from 1 to 7.

6. The pharmaceutical composition according to claim 5, wherein m is 7.

7. The pharmaceutical composition according to claim 1, further comprising a pharmaceutically acceptable vehicle.

* * * * *